United States Patent
DePietro et al.

(10) Patent No.: US 10,212,986 B2
(45) Date of Patent: Feb. 26, 2019

(54) SYSTEM, APPAREL, AND METHOD FOR IDENTIFYING PERFORMANCE OF WORKOUT ROUTINES

(71) Applicant: General Instrument Corporation, Horsham, PA (US)

(72) Inventors: Mark G. DePietro, Harleysville, PA (US); Stewart M. Wiener, Oreland, PA (US)

(73) Assignee: ARRIS Enterprises LLC, Suwanee, GA (US)

(*) Notice: Subject to any disclaimer, the term of this patent is extended or adjusted under 35 U.S.C. 154(b) by 0 days.

(21) Appl. No.: 13/723,157

(22) Filed: Dec. 20, 2012

(65) Prior Publication Data

US 2014/0163704 A1    Jun. 12, 2014

Related U.S. Application Data

(60) Provisional application No. 61/735,010, filed on Dec. 9, 2012.

(51) Int. Cl.
   *G06F 19/00* (2018.01)
   *A63B 24/00* (2006.01)
   (Continued)

(52) U.S. Cl.
   CPC ............ *A43B 3/0005* (2013.01); *G01S 19/19* (2013.01); *G06F 19/00* (2013.01);
   (Continued)

(58) Field of Classification Search
   CPC .......... A63B 24/00; A63B 21/00; A63B 22/00
   (Continued)

(56) References Cited

U.S. PATENT DOCUMENTS

| 4,337,049 A | 6/1982 | Connelly |
| 5,848,396 A | 12/1998 | Gerace |

(Continued)

FOREIGN PATENT DOCUMENTS

| WO | 2010033346 A2 | 3/2010 |
| WO | 2010129165 A2 | 11/2010 |
| WO | 2012136462 A1 | 10/2012 |

OTHER PUBLICATIONS

"Detecting Ventilatory Threshold with BioHarness™" Zephyr Technology, pp. 2 (2008).

(Continued)

*Primary Examiner* — James S McClellan
*Assistant Examiner* — Syvila Weatherford
(74) *Attorney, Agent, or Firm* — Stewart M. Wiener

(57) ABSTRACT

A system for automatically identifying performance of workout routines is provided. The system includes a set of sensors wearable on a body of an exerciser during performance of exercises. Each sensor is configured to measure a parameter selected from motion, acceleration, position, and applied force, and to communicate parameters measured. The system also includes a device configured to receive a set of parameters measured over a period of time by the set of sensors and to access stored pattern information corresponding to a plurality of predetermined exercise activities and a plurality of predetermined workout routines to identify one or more performed exercise activities performed by the exerciser and to identify a performed workout routine performed by the exerciser during the period of time. Apparel and methods are also disclosed.

44 Claims, 6 Drawing Sheets

(51) Int. Cl.
*A43B 3/00* (2006.01)
*G01S 19/19* (2010.01)
*H04L 29/08* (2006.01)
*A61B 5/00* (2006.01)
*A61B 5/11* (2006.01)

(52) U.S. Cl.
CPC ........ *G06F 19/3481* (2013.01); *H04L 67/125* (2013.01); *A61B 5/0024* (2013.01); *A61B 5/11* (2013.01); *A63B 24/00* (2013.01)

(58) Field of Classification Search
USPC .............................................. 482/8; 473/570
See application file for complete search history.

(56) References Cited

U.S. PATENT DOCUMENTS

| | | | |
|---|---|---|---|
| 6,005,597 | A | 12/1999 | Barrett et al. |
| 6,311,194 | B1 | 10/2001 | Sheth et al. |
| 6,381,482 | B1 | 4/2002 | Jayaraman et al. |
| 6,701,362 | B1 | 3/2004 | Subramonian et al. |
| 6,727,914 | B1 | 4/2004 | Gutta |
| 6,769,066 | B1 | 7/2004 | Botros et al. |
| 6,801,909 | B2 | 10/2004 | Delgado et al. |
| 6,839,680 | B1 | 1/2005 | Liu et al. |
| 6,955,542 | B2 | 10/2005 | Roncalez et al. |
| 6,970,731 | B1 | 11/2005 | Jayaraman et al. |
| 6,988,093 | B2 | 1/2006 | Pic et al. |
| 7,043,552 | B2 | 5/2006 | Davis |
| 7,285,090 | B2 | 10/2007 | Stivoric et al. |
| 7,421,369 | B2 | 9/2008 | Clarkson |
| 7,505,951 | B2 | 3/2009 | Thompson et al. |
| 7,599,955 | B2 | 10/2009 | Yoon et al. |
| 7,620,894 | B1 | 11/2009 | Kahn |
| 7,797,672 | B2 | 9/2010 | Thompson et al. |
| 7,801,896 | B2 | 9/2010 | Szabo |
| 7,818,329 | B2 | 10/2010 | Campbell et al. |
| 7,865,354 | B2 | 1/2011 | Chitrapura et al. |
| 7,870,489 | B2 | 1/2011 | Serita et al. |
| 7,877,345 | B2 | 1/2011 | Nigam et al. |
| 7,962,529 | B1 | 6/2011 | Datar et al. |
| 8,033,959 | B2 | 10/2011 | Oleson et al. |
| 8,033,996 | B2 | 10/2011 | Behar |
| 8,090,727 | B2 | 1/2012 | Lachtarnik et al. |
| 8,137,270 | B2 | 3/2012 | Keenan et al. |
| 8,145,648 | B2 | 3/2012 | Kunjithapatham et al. |
| 8,185,487 | B2 | 5/2012 | Tuzhilin et al. |
| 8,200,323 | B2 | 6/2012 | DiBenedetto et al. |
| 8,200,477 | B2 | 6/2012 | Yi et al. |
| 8,335,803 | B2 | 12/2012 | Abraham |
| 8,356,025 | B2 | 1/2013 | Cai et al. |
| 8,428,357 | B2 | 4/2013 | Stephenson |
| 8,478,712 | B2 | 7/2013 | Thompson et al. |
| 8,620,964 | B2 | 12/2013 | Tsatsou et al. |
| 8,838,435 | B2 | 9/2014 | Talley et al. |
| 8,935,305 | B2 | 1/2015 | Novak et al. |
| 8,943,015 | B2 | 1/2015 | Davis et al. |
| 2002/0078090 | A1 | 6/2002 | Hwang et al. |
| 2002/0184080 | A1 | 12/2002 | Murad et al. |
| 2003/0018616 | A1 | 1/2003 | Wilbanks et al. |
| 2003/0028871 | A1 | 2/2003 | Wang et al. |
| 2003/0078811 | A1 | 4/2003 | Cole et al. |
| 2003/0105658 | A1 | 6/2003 | Chen et al. |
| 2004/0039564 | A1 | 2/2004 | Mueller |
| 2004/0205648 | A1 | 10/2004 | Tinsley et al. |
| 2004/0249866 | A1 | 12/2004 | Chen et al. |
| 2005/0034107 | A1 | 2/2005 | Kendall et al. |
| 2005/0071328 | A1 | 3/2005 | Lawrence |
| 2005/0091038 | A1 | 4/2005 | Yi et al. |
| 2005/0138177 | A1 | 6/2005 | Davis |
| 2005/0149494 | A1 | 7/2005 | Lindh et al. |
| 2005/0188408 | A1 | 8/2005 | Wallis et al. |
| 2006/0053172 | A1 | 3/2006 | Gardner et al. |
| 2006/0200341 | A1 | 9/2006 | Corston-Oliver et al. |
| 2006/0218651 | A1 | 9/2006 | Ginter et al. |
| 2007/0053513 | A1 | 3/2007 | Hoffberg |
| 2007/0115979 | A1 | 5/2007 | Balay et al. |
| 2007/0130350 | A1 | 6/2007 | Alperovitch et al. |
| 2008/0005313 | A1 | 1/2008 | Flake et al. |
| 2008/0021700 | A1 | 1/2008 | Moitra et al. |
| 2008/0036917 | A1 | 2/2008 | Pascarella et al. |
| 2008/0077614 | A1 | 3/2008 | Roy |
| 2008/0133488 | A1 | 6/2008 | Bandaru et al. |
| 2008/0177721 | A1 | 7/2008 | Agarwal et al. |
| 2008/0275694 | A1 | 11/2008 | Varone |
| 2008/0320553 | A1 | 12/2008 | Balay et al. |
| 2009/0112910 | A1 | 4/2009 | Picault et al. |
| 2009/0198642 | A1 | 8/2009 | Akkiraju et al. |
| 2009/0233770 | A1* | 9/2009 | Vincent et al. ................... 482/8 |
| 2009/0234711 | A1 | 9/2009 | Ramer et al. |
| 2009/0234878 | A1 | 9/2009 | Herz et al. |
| 2009/0259459 | A1 | 10/2009 | Ceusters et al. |
| 2009/0328133 | A1 | 12/2009 | Strassner et al. |
| 2010/0017819 | A1 | 1/2010 | Gerbrandt et al. |
| 2010/0030552 | A1 | 2/2010 | Chen et al. |
| 2010/0050118 | A1 | 2/2010 | Chowdhury et al. |
| 2010/0063779 | A1* | 3/2010 | Schrock et al. .............. 702/188 |
| 2010/0088151 | A1 | 4/2010 | Kim et al. |
| 2010/0122178 | A1 | 5/2010 | Konig et al. |
| 2010/0125483 | A1 | 5/2010 | Davis et al. |
| 2010/0125543 | A1 | 5/2010 | Thompson et al. |
| 2010/0191582 | A1 | 7/2010 | Dicker et al. |
| 2010/0235908 | A1 | 9/2010 | Eynon et al. |
| 2010/0274100 | A1 | 10/2010 | Behar et al. |
| 2010/0281025 | A1 | 11/2010 | Tsatsou et al. |
| 2010/0283630 | A1 | 11/2010 | Alonso |
| 2010/0293221 | A1 | 11/2010 | Sidman et al. |
| 2010/0318542 | A1 | 12/2010 | Davis |
| 2011/0052005 | A1 | 3/2011 | Selner |
| 2011/0054270 | A1 | 3/2011 | Derchak |
| 2011/0087670 | A1 | 4/2011 | Jorstad et al. |
| 2011/0092337 | A1* | 4/2011 | Srinivasan et al. ............... 482/8 |
| 2011/0137906 | A1 | 6/2011 | Cal et al. |
| 2011/0153042 | A1 | 6/2011 | Burton et al. |
| 2011/0179084 | A1 | 7/2011 | Waddington et al. |
| 2011/0249953 | A1 | 10/2011 | Suri et al. |
| 2011/0256983 | A1 | 10/2011 | Malack et al. |
| 2012/0041959 | A1 | 2/2012 | Weissman et al. |
| 2012/0156991 | A1 | 6/2012 | Burton et al. |
| 2012/0157263 | A1 | 6/2012 | Sivak et al. |
| 2012/0323496 | A1* | 12/2012 | Burroughs et al. ............. 702/19 |
| 2013/0132442 | A1 | 5/2013 | Tsatsou et al. |
| 2013/0166494 | A1 | 6/2013 | Davis et al. |
| 2013/0166605 | A1 | 6/2013 | Li et al. |
| 2013/0166609 | A1 | 6/2013 | Hao et al. |
| 2013/0179149 | A1 | 7/2013 | Talley et al. |
| 2013/0179467 | A1 | 7/2013 | Ain |
| 2013/0232145 | A1 | 9/2013 | Weissman et al. |
| 2013/0254140 | A1 | 9/2013 | Li et al. |
| 2013/0304469 | A1 | 11/2013 | Kamada et al. |
| 2013/0346414 | A1 | 12/2013 | Smith et al. |
| 2013/0347056 | A1 | 12/2013 | Kuhlman et al. |
| 2013/0347057 | A1 | 12/2013 | Hurwitz et al. |
| 2014/0026184 | A1 | 1/2014 | Pergament et al. |
| 2014/0089967 | A1 | 3/2014 | Mandalia et al. |
| 2014/0095608 | A1 | 4/2014 | Mandalia et al. |
| 2014/0107817 | A1* | 4/2014 | Ellis et al. ....................... 700/91 |
| 2014/0147819 | A1* | 5/2014 | Cricchio et al. .............. 434/238 |
| 2014/0161322 | A1 | 6/2014 | Cheng et al. |
| 2014/0173075 | A1 | 6/2014 | Liu et al. |
| 2014/0176604 | A1 | 6/2014 | Venkitaraman et al. |
| 2014/0181160 | A1 | 6/2014 | Novak et al. |
| 2014/0200906 | A1 | 7/2014 | Bentley et al. |
| 2014/0258204 | A1 | 9/2014 | Liu et al. |
| 2014/0266782 | A1 | 9/2014 | You et al. |
| 2014/0280138 | A1 | 9/2014 | Li et al. |
| 2014/0280529 | A1 | 9/2014 | Davis et al. |
| 2015/0032682 | A1 | 1/2015 | You et al. |

OTHER PUBLICATIONS

"Fitbit Product Manual," last update on Mar. 29, 2010, pp. 23.
"Monitoring Under-training with the Zephyr PSM System," Zephyr Technology (2010).

(56) References Cited

OTHER PUBLICATIONS

"Nike + iPod Meet your new personal trainer," accessed http://www.apple.com/ipod/nike/, accessed on Jul. 15, 2011, pp. 7.
"Nike + iPod User Guide," Apple Inc, pp. 32 (2010).
"Nike+ Basketball-Training," Guide, pp. 16.
"Nike+ SportWatch GPS," Quick Start Guide, pp. 42.
"OmniSense Falconview Integration," Zephyr Technology, pp. 2 (2011).
"Personal Health," accessed at http://www.proetex.org/final%20proetex%20learning/personal_health.htm, accessed on Jan. 15, 2013, pp. 7.
"Sports and Training," accessed at http://www.proetex.org/final%20proetex%20learning/Sports.htm, accessed on Jan. 15, 2013, pp. 3.
"Validity of BioHarness™ Heart Rate vs 3-lead ECG," Zephyr Technology, pp. 2 (2008).
Amft, O., et al., "Recognition of user activity sequences using distributed event detection," vol. 4793, Springer-Verlag, pp. 126-141 (2007).
Bai, J., et al., "Movelets: A dictionary of movement," Electronic Journal of Statistics, vol. 6, pp. 559-578 (2012).
Brezmes, T., et al., "Activity Recognition from Accelerometer Data on a Mobile Phone," Distributed Computing, Artificial Intelligence, Bioinformatics, Soft Computing, and Ambient Assisted Living, Lecture Notes in Computer Science, pp. 796-799 (2009).
Brezmes, T., et al., "User activity monitoring using conventional cell phones for IMCIC 2010," International Multi Conference on Complexity, Informatics and Cybernetics (IMCIC 2010), International Institute of Informatics and Systemics (IIIS), pp. 3 (Apr. 2010).
Cinaz, B., et al., "Towards Continuous Monitoring of Mental Workload," 5th International Workshop on Ubiquitous Health and Wellness, pp. 5, ACM (2010).
Collette, M., "With tentacles in many disciplines, capstone team merges engineering, design," accessed at http://www.northeastern.edu/news/2012/01/squid/, dated Jan. 4, 2012, pp. 3.
Electricfoxy, "Move: Precision in Movement," accessed at www.electricfoxy.com/move/index.html, accessed on Sep. 10, 2012, pp. 3.
Georgia Tech, "Georgia Tech researchers develop first "woven computer"," accessed at Www.smartshirt.gatech.edu/images/wear html, accessed on Jan. 15, 2012, pp. 2.
John, D., et al., "Calibrating a novel multi-sensor physical activity measurement system," Physiological Measurement, vol. 32, No. 9, pp. 1473-1489, Institute of Physics and Engineering in Medicine (2011).
Kasteren, T.V., et al., "Accurate Activity Recognition in a Home Setting," Proceedings of the 10th international conference on Ubiquitous computing, pp. 1-9 (2008).
Kerr, W. et al., "Activity Recognition with Finite State Machines," Proceedings of the Twenty-Second international joint conference on Artificial Intelligence, vol. 2, pp. 1348-1353 (2011).
Lampert, C.H., et al., "Learning to Detect Unseen Object Classes by Between-Class Attribute Transfer," IEEE Conference on Computer Vision and Pattern Recognition, pp. 951-958 (2009).
Lester, J., et al., "A Practical Approach to Recognizing Physical Activities," Pervasive Computing of the 4th International Conference, Springer-Verlag, pp. 1-16 (2006).
Maurer, U., et al., "Activity Recognition and Monitoring Using Multiple Sensors on Different Body Positions," Proceedings of the International Workshop on Wearable and Implantable Body Sensor Networks (BSN'06), IEEE, pp. 5 (2006).
Morris, S.J., et al., "A Compact Wearable Sensor Package for Clinical Gait Monitoring," Offspring, vol. 1, No. 1, pp. 7-15, Massachusetts Institute of Technology (2002).
Palatucci, M., et al., "Zero-Shot Learning with Semantic Output Codes," Neural Information Processing Systems, pp. 1-9 (2009).
Pärkkä, J., et al., "Activity Classification Using Realistic Data From Wearable Sensors," IEEE Tranactions on Information Technology in Biomedicine, vol. 10, No. 1, pp. 119-128, (Jan. 2006).
Philipose, M., et al., "The Probabilistic Activity Toolkit: Towards Enabling Activity-Aware Computer Interfaces," Intel Corporation, pp. 1-8 (2003).
Ravi, N., et al., "Activity Recognition from Accelerometer Data", Proceedings, The 20th National Conference on Artificial Intelligence and the 17th Innovative Applications of Artificial Intelligence Conference, pp. 1541-1546, American Association for Artificial Intelligence (2005).
Roggen, D., et al., "Collecting complex activity datasets in highly rich networked sensor environments," Proceedings of the Seventh International Conference on Networked Sensing Systems (INSS), pp. 8 (2010).
Schwarz, L.A., et al., "Multiple-Activity Human Body Tracking in Unconstrained Environments," Proceedings of the 6th international conference on Articulated motion and deformable objects, pp. 10 (2010).
Sorber, J., et al., "An Amulet for Trustworthy Wearable mHealth," roceedings of the Twelfth Workshop on Mobile Computing Systems & Applications, pp. 6, ACM (2012).
Stack, K., "In-Chest Sensors Gather Data on NFL Prospects," accessed at http://www.wired.com/playbook/2011/02/nfl-combine-chest-sensors/all/1, dated Feb. 23, 2011, pp. 11.
Stikic, M., et al., "Weakly supervised recognition of daily life activities with wearable sensors," IEEE Transactions on Pattern Analysis and Machine Intelligence, vol. 33, Issue 12, pp. 2521-2537 (2011).
Sung, M., et al, "A Shiver Motion and Core Body Temperature Classification for Wearable Soldier Health Monitoring Systems," 9th IEEE International Symposium of Wearable Computers (ISWC'04), vol. 1, pp. 4 (2004).
Sung, M., et al, "LiveNet: Health and Lifestyle Networking Through Distributed Mobile Devices," Workshop on Applications of Mobile Embedded Systems (WAMES '04) at Mobisys '04, pp. 3 (2004).
Sung, M., et al., "Minimally-Invasive Physiological Sensing for Human-Aware Interfaces," HCI International, pp. 10, ACM (2005).
Sung, M., et al., "Wearable Feedback Systems for Rehabilitation", Journal of NeuroEngineering and Rehabilitation, pp. 12 (2005).
Varkey, J.P., et al., "Human motion recognition using a wireless sensor-based wearable system," vol. 16, Issue 7, pp. 897-910 (2012).
Varkey, J.P., et al., "Movement Recognition Using Body Area Networks," IEEE Global Telecommunications Conference, pp. 6 (2009).
Woyke, E., "AT&T Plans to Sell Health-Tracking Clothing," accessed at www.forbes.com/sites/elizabethwoyke/2011/10/28/att-plans-to-sell-health-tracking-clothing/print/, dated Oct. 28, 2011, pp. 2.
NIKE, "The Nike+ FuelBand User's Guide", URL: support-en-us.nikeplus.com/ci/fattach/get/276180/0/filename/FuelBand_Manual_Online_ENG_edit12b_rev.pdf, accessed Jan. 18, 2013, last updated Nov. 2012.
Heng-Tze Cheng, et al. "Nuactiv: Recognizing unseen new activities using semantic attribute-based learning." In Proceedings of the 11th Annual International Conference on Mobile Systems, Applications, and Services, pp. 361-374. ACM, Jun. 2013.
Heng-Tze Cheng, et al. "Towards zero-shot learning for human activity recognition using semantic attribute sequence model." In Proceedings of the 2013 ACM International Joint Conference on Pervasive and Ubiquitous computing, pp. 355-358. ACM, Sep. 2013.
Heng-Tze Cheng, "Learning and Recognizing the Hierarchical and Sequential Structure of Human Activities." Carnegie Mellon University: Dissertations (Paper 293). Dec. 2013.
Saad, et al., "An Ontology for Video Human Movement Representation based on Benesh Notation", IEEE, May 2012, hereinafter Saad.
Raheb, et al., "A Labanotation Based Ontology for Representing Dance Movement", IEEE, 2011, hereinafter Raheb.

\* cited by examiner

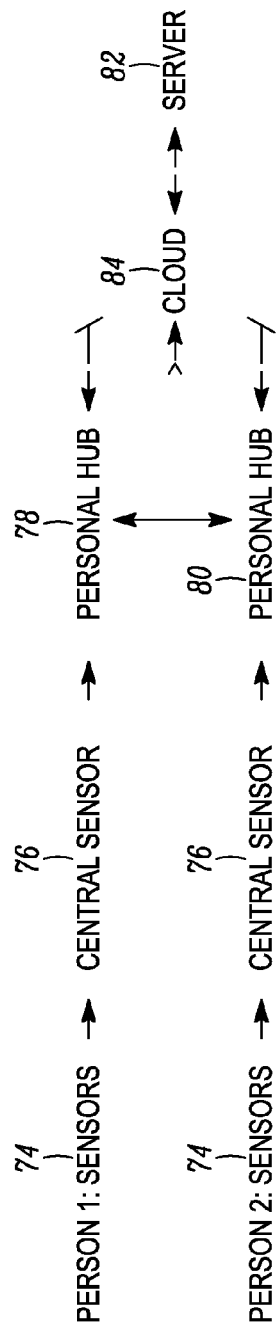
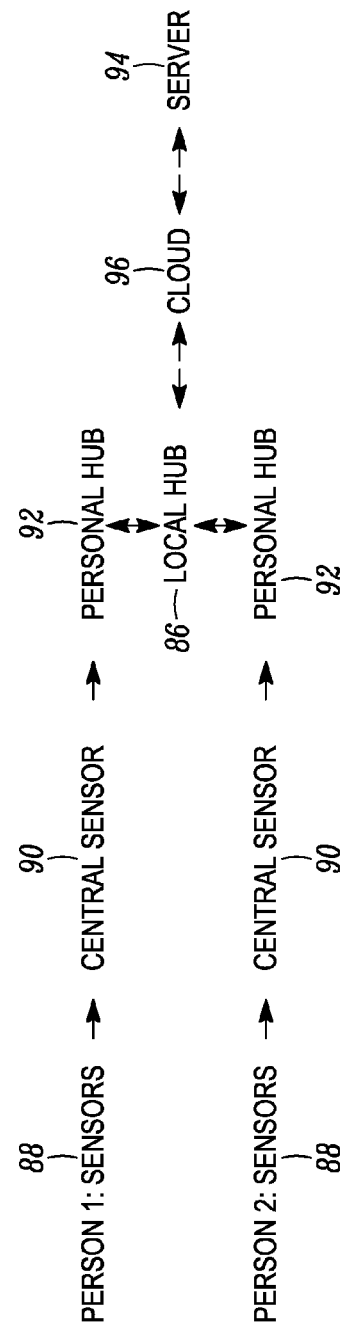

SYSTEM, APPAREL, AND METHOD FOR IDENTIFYING PERFORMANCE OF WORKOUT ROUTINES

BACKGROUND

Various electronic apparatus and devices are used for automatically tracking and recording the movements of a human body during a physical activity such as a sporting activity or other health-related activity. The purpose of such apparatus and devices can be to eliminate the need of the person performing the activity or another person to manually track and record the accomplishment of a particular physical activity, such as the completion of an exercise.

By way of example, fitness centers may have weight lifting machines and circuits of such machines where each machine is designed for an exerciser to use in performing a pre-determined, known, well-defined, single exercise. Each weight lifting machine may have electronics permitting a user to automatically track and record the user's use of the particular machine on a particular date, the amount of weight lifted by the user during the exercise, the number of sets of the exercise performed on the machine by the user, and the number of repetitions within each set performed by the user. Such electronics may also be used to store proper settings for the user relative to the machine, for instance, proper seat height and the like. The electronics may further provide feedback during performance of the exercise, such as, providing an indication when the user's motions are considered too rapid for the exercise or when the user has reached a set goal.

Another example of physical activity tracking and recording devices are those that are worn directly on the body of the exerciser. Such devices may include sensors, heart-rate monitors, GPS units or watches, and like electronics and may be used alone or in connection with other apparatus (i.e., treadmills, etc.) to automatically track and record parameters such as distance traversed, elapsed time, pace, amount of calories burned, heart rate, and the like of the user relative to a known exercise.

BRIEF DESCRIPTION OF THE DRAWINGS

Various features of the embodiments described in the following detailed description can be more fully appreciated when considered with reference to the accompanying figures, wherein the same numbers refer to the same elements.

FIG. 4 is a diagram showing a flow of communication between wearable sensors worn on competing exercisers to a remote server in accordance with an embodiment.

FIG. 5 is a diagram showing a flow of communication between wearable sensors worn on competing exercisers to a local hub and remote server in accordance with an embodiment.

DETAILED DESCRIPTION

Figure 1:
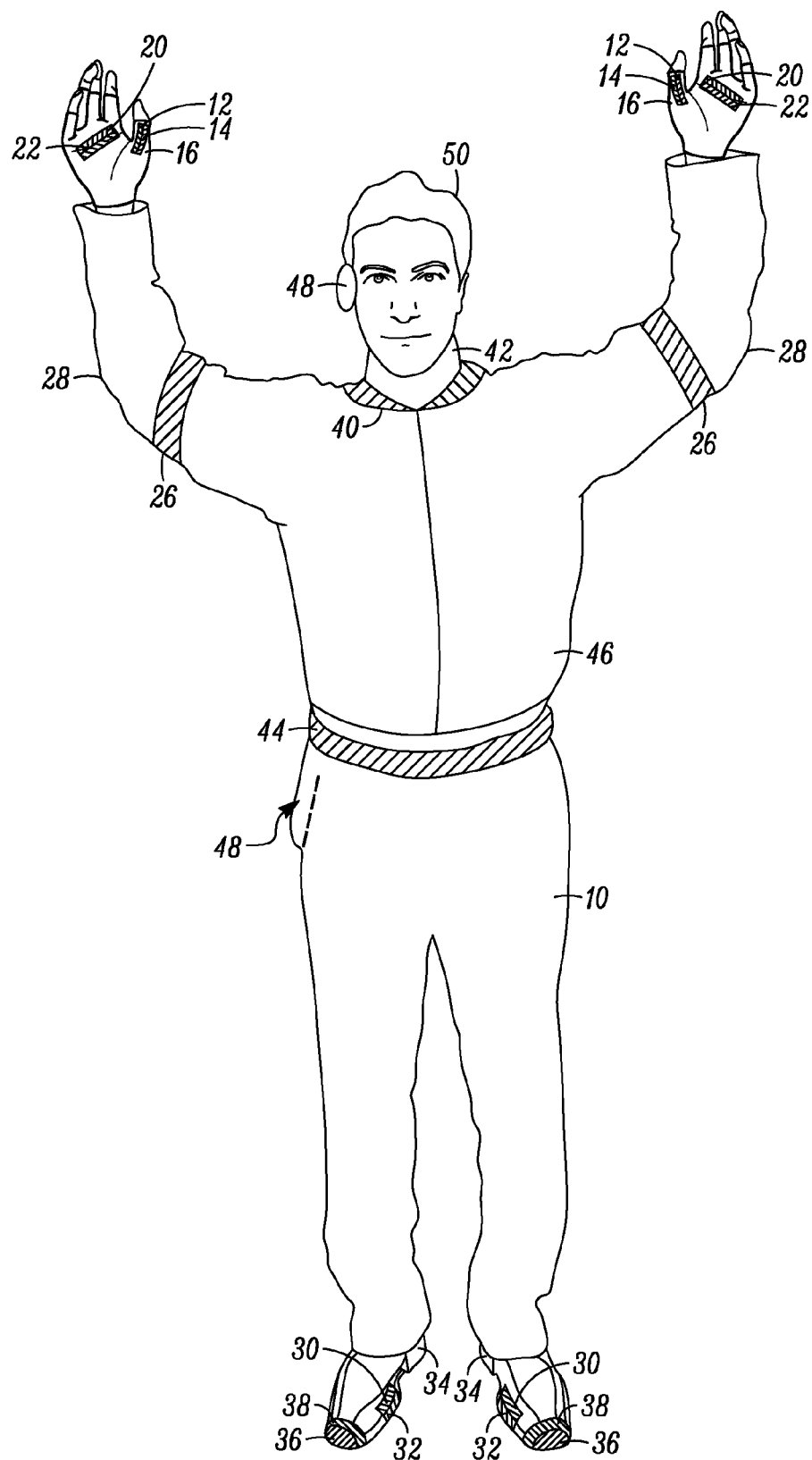
FIG. 1 is an elevational view of an exerciser wearing an arrangement of sensors and a personal hub device in accordance with an embodiment.

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In some instances, well known methods and structures have not been described in detail so as not to unnecessarily obscure the embodiments.

Embodiments are disclosed herein with respect to systems, devices, apparel, and methods for use in automatically identifying particular exercise activities and workout routines from various different exercise activities and workout routines and for recording performance related data with respect to the performance of a particular set or sequence of physical activities or with respect to the performance of a particular workout routine. With these embodiments, manual recording of such data is eliminated and an exerciser is free to perform any number of entirely different exercisers or exercise routines or workouts without having to manually record or identify the exercises, the workouts or routines, or the results of such exercises, or utilize different devices for each different exercise performed.

In this disclosure, the term "calisthenics" is used to refer to rhythmic body exercises in which the exerciser's own body weight is used as the resistance for the exercise. Examples of calisthenics may include push-ups, pull-ups, sit-ups, rope climbing, and the like. The term "free-weight exercise" refers to an exercise in which a dumb bell or other form of weighted object that is not connected to, controlled by, or balanced by other apparatus or machinery is freely lifted, controlled and balanced by the exerciser and provides the resistance for the exercise. Further, the terms "exercise routine", "exercise workouts", and "workout routines" as used herein refer to a predetermined sequence of a set of exercises with or without intervals of rest therebetween. While the embodiments disclosed herein may relate to automatically and electronically identifying and tracking the performance of different calisthenics, free-weight exercises, and workout routines, it should be understood that any physical activities could also be automatically tracked and recorded via use of the systems, devices, apparel, and methods disclosed herein.

In one embodiment, a system for automatically identifying performance of workout routines is provided. The system includes a set of sensors each being wearable at one or more specified locations on a body of an exerciser during performance of a plurality of exercises. Each of the sensors is configured to measure a parameter selected from a group consisting of motion, acceleration, position relative to one or more others of the set of sensors, and applied force, and each of the sensors is configured to communicate parameters measured. The system also includes a device configured to receive a set of parameters measured over a period of time by the set of sensors and to access stored pattern information corresponding to a plurality of predetermined exercise activities and a plurality of predetermined workout routines to identify one or more performed exercise activities performed by the exerciser during the period of time based on the stored pattern information and the set of parameters measured over at least a portion of the period of time. The device is further configured to identify a performed workout routine performed by the exerciser during the period of time based on the stored pattern information and the performed exercise activities.

In other embodiments disclosed herein, exercise apparel for use in automatically identifying workout routines is provided. The apparel can include an article of handwear carrying a set of sensors each being wearable on a hand of an exerciser during performance of exercises, configured to measure a parameter selected from motion, acceleration, position, and applied force, and configured to wirelessly communicate parameters measured. The apparel can also include an article of footwear carrying a set of sensors each being wearable on a foot of an exerciser during performance of exercises, configured to measure a parameter selected from motion, acceleration, position, and applied force, and configured to wirelessly communicate parameters measured. At least one of the set of sensors being carried on the footwear may be located in a position selected from a front tip of the footwear, a side of the footwear, and a top front of the footwear.

In a still further embodiment, a method for automatically identifying performance of workout routines is provided. The method includes the step of measuring a set of parameters with a set of sensors each being worn at one or more specified locations on a body of an exerciser during performance of a plurality of exercises. Each of the sensors is configured to measure a parameter selected from a group consisting of motion, acceleration, position relative to one or more others of said set of sensors, and applied force, and each of the sensors is configured to communicate parameters measured. The method further includes a step of communicating a set of parameters measured over a period of time by the set of sensors to a device configured to access stored pattern information corresponding to a plurality of predetermined exercise activities and a plurality of predetermined workout routines. The method also includes a step of analyzing the set of parameters with the device via pattern recognition to identify one or more performed exercise activities performed by the exerciser during the period of time and to identify a performed workout routine performed by the exerciser during the period of time.

The above embodiments utilize wearable sensors located at one or more specified locations on the body of the exerciser for purposes of identifying specific exercises and/or specific workouts or routines based on motion, acceleration, force applied, and/or relative positioning of the sensors. Each exercise or other physical activity is automatically identified based on readings or measurements taken by the wearable sensors and based on the particular location of the sensors on the body of the exerciser. This captured data enables the embodiments to provide analysis, recording, reporting, coaching, competitive features, and like information to the exerciser and/or other interested entity. Further, the data also enables authentication of performance of particular exercise routines or workouts that may comprise the performance of multiple different exercises performed in sequence.

Different individual exercises such as calisthenics or free-weight exercises as well as rest periods between exercises may be identified from readings taken by force, motion, acceleration or position sensors worn on the hands, palms, thumbs, fingers, feet, arms, elbows, neck, back, buttocks, and/or trunk of the exerciser. Numerous different exercises and a pattern of such exercises and any rest period between exercises can be identified from the readings captured by the various sensors on the body of the exerciser via use of pattern recognition techniques. Thus, the exercise and pattern or sequence of exercises being performed is automatically and electronically identified based on sensor readings captured relative to position, force, acceleration and/or motion of different body parts of the exerciser and based on a comparison relative to known exercise and workout routine profiles that may be stored in the form of database entries within an electronic library of profiles.

By way of example of a specific exercise activity, a particular activity that may be performed by the exerciser may be a push-up. A known or expected profile for a push-up may include sensor readings indicating: continuous weight on hands and front of toes; no weight on soles of feet; elbows remain mostly fixed; trunk moves up and down; and feet remain relatively stationary. Thus, if data captured by sensors worn on the hands, feet, elbows and trunk of the exerciser correspond to the above referenced expected profile of a push-up, the data can be electronically analyzed, compared and matched to the profile of a push-up, and automatically recorded as a push-up. In addition, the number of times the sensors indicate that the trunk moves up and down during the identified push-up can be used to automatically determine and record the number of push-ups performed by the exerciser. Of course, elapsed time, pace, force required to perform a push-up, calories burned, heart rate, and like information can also be obtained from the sensor data, as desired.

As another example, the activity being performed by the exerciser may be an exercise known as a squat. A known or expected profile for a squat exercise may include sensor readings indicating: trunk moves up and down; weight increases on bottom of feet; and upper arm above elbow joint remains relatively fixed in position with respect to trunk and moves up and down with trunk. Thus, if data captured by sensors worn on the feet, trunk and arms of the exerciser correspond to the above referenced expected profile of a squat exercise, the data can be electronically analyzed, compared and matched to the profile of a squat, and the exercise can be automatically identified and recorded as a squat. In addition, the number of times the sensors indicate that the trunk moves up and down during the identified squat exercise can be used to automatically determine and record the repetitions performed by the exerciser. Of course, elapsed time, pace, force required to perform a squat, calories burned, heart rate, and like information can also be obtained from the sensor data, as desired.

As a further example of an exercise activity, the activity performed by the exerciser may be a press. A known or expected profile for a press exercise may include sensor readings indicating: trunk is fixed; weight on bottom of feet; elbows move up and down; significant weight on palms; and weight on thumbs or fingers. Thus, if data captured by sensors worn on the trunk, feet, elbows and hands of the exerciser correspond to the above referenced expected profile of a press exercise, the data can be electronically analyzed, compared and matched to the profile of a press, and the exercise can be automatically identified and recorded as a press. In addition, the number of times the sensors indicate that the elbows move up and down during the identified press exercise can be used to automatically determine and record the repetitions performed by the exerciser within a particular set. Of course, elapsed time, pace, force required to perform a press, calories burned, heart rate, and like information can also be obtained from the sensor data, as desired.

As still a further example of an exercise activity, the activity being performed by the exerciser may be a pull up. A known or expected profile for a pull-up may include sensor readings indicating: no weight on feet; significant weight on palm (and/or bottom third of fingers); elbows move up and down; and trunk moves up and down to a greater extent relative to elbows. Thus, if data captured by sensors worn on the feet, hands, elbows and trunk of the exerciser correspond to the above referenced expected profile of a pull-up, the data can be electronically analyzed, compared and matched to the profile of a pull-up, and the exercise can be automatically identified and recorded as a pull-up. In addition, the number of times the sensors indicate that the elbows and/or trunk move up and down during the identified pull-up exercise can be used to automatically determine and record the repetitions performed by the exerciser within a particular set. Of course, elapsed time, pace, force required to perform a pull-up, calories burned, heart rate, and like information can also be obtained from the sensor data, as desired.

While a few examples of calisthenics and/or free-weight exercises have been described above, it naturally follows that these examples are not limiting and that profiles can be identified for any number of different calisthenics and/or free-weight exercises so that any number of different physical activities and exercises can be automatically identified and distinguished from other physical activities and exercises. Thus, based on a collection of readings taken by the multiple sensors worn by the exerciser during the performance of a particular exercise and based on a comparison of the collection of readings to numerous different stored profiles of exercises that may be stored in a database, memory, or the like, an exercise or other physical activity can be automatically detected without any intervention of the exerciser or other person before, during or after performance of the exercise.

In addition to automatically detecting, identifying and recording the performance of individual exercises, embodiments are provided which automatically identify and record known workout routines by stitching together in sequence individually identified exercises with or without intervals of rest periods. Still further, embodiments are provided which detect and distinguish among different types of workout routines performed as part of a fitness program. For example, a workout routine may be a type having a task priority or a type having a time priority. The embodiments distinguish among the above referenced exercise types by making inferences based on detected activity, detected elapsed time, and based on whether a previously detected pattern or round of exercises is complete or incomplete in its final iteration.

For purposes of example of a workout routine, a workout routine referred to as a "FRAN" may be known to include the following sequence of exercises and repetitions: twenty-one (21) thrusters, followed by twenty-one (21) pull-ups, followed by fifteen (15) thrusters, followed by fifteen (15) pull-ups, followed by nine (9) thrusters, followed by nine (9) pull-ups. A "thruster" is an exercise performed with a free-weight that is a combination of a squat and a press such that, as the exerciser returns the trunk to the upper position following a squat, the exerciser precisely times the performance of a press with the free weight. The disclosure of a FRAN workout routine is merely for purposes of example, and there are many different workout routines having different combinations of exercises, sequence of exercises, and repetitions for each exercise that may comprise a workout routine and may be detected by the embodiments.

With respect to an exerciser's performance of the above described FRAN workout routine used for purposes of example, the collection of readings captured by the sensors during this workout can be compared to profiles of individual exercises to identify the performance of alternating sets of thrusters and pull-ups and the repetitions performed by the exerciser within each set. The automatic identification of the exercises in sequence and repetitions performed for each exercise within a period of time can be compared to known profiles of workout routines and thus permit a workout routine, such as a FRAN, to be identified and distinguished from other workout routines stored in a database.

Accordingly, not only do the embodiments identify and record individually performed exercises and repetitions performed, the embodiments disclosed herein can also be used to identify and record the performance of exercise workout routines by the exerciser. This enables an exerciser to compare his/her performance today, for instance, of a FRAN exercise with any of his/her past performances or with the performances of others based on elapsed time for the total workout and for each exercise within the sequence, pace of exercise for each exercise in the sequence, amount of weight lifted, and the like.

Figure 6:
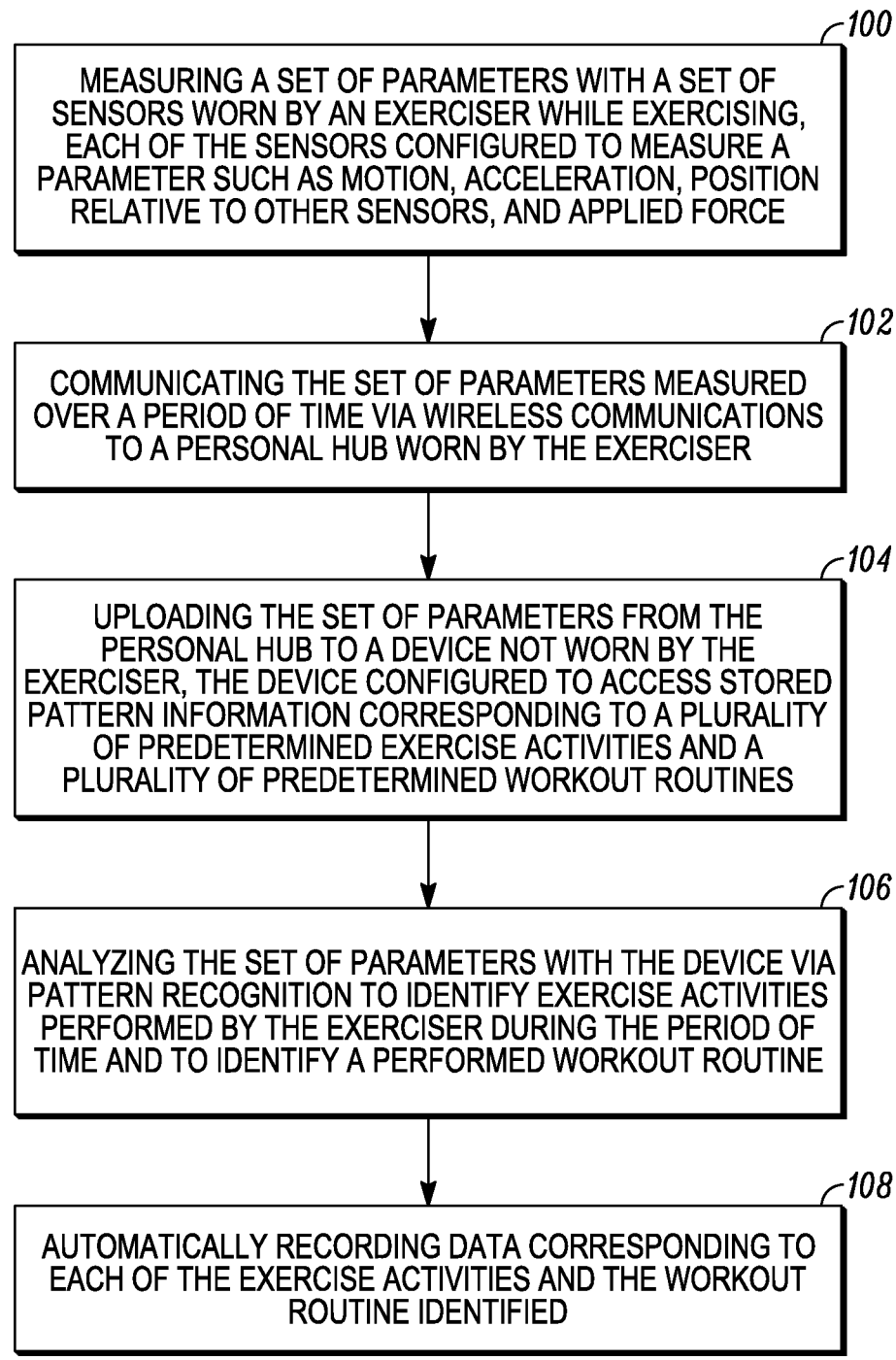
FIG. 6 is a flow diagram of process steps for a method of automatically identifying the performance of a workout routine by an exerciser in accordance with an embodiment.

By way of example, FIG. 6 provides an embodiment of a method for automatically identifying performance of a workout routine. A set of parameters is measured in step 100 with a set of sensors worn by an exerciser while exercising, each of the sensors being configured to measure a parameter such as motion, acceleration, position relative to other sensors, and applied force. The set of parameters measured over a period of time are communicated in step 102 via wireless communications to a personal hub worn by the exerciser. The set of parameters may be uploaded in step 104 from the personal hub to a device not worn by the exerciser, the device being configured to access stored pattern information corresponding to a plurality of predetermined exercise activities and a plurality of predetermined workout routines. The set of parameters can be analyzed in step 106 with the device via pattern recognition to identify exercise activities performed by the exerciser during the period of time and to identify a performed workout routine. Data corresponding to each of the exercise activities and the workout routine identified can be automatically recorded in step 108.

Figure 9:
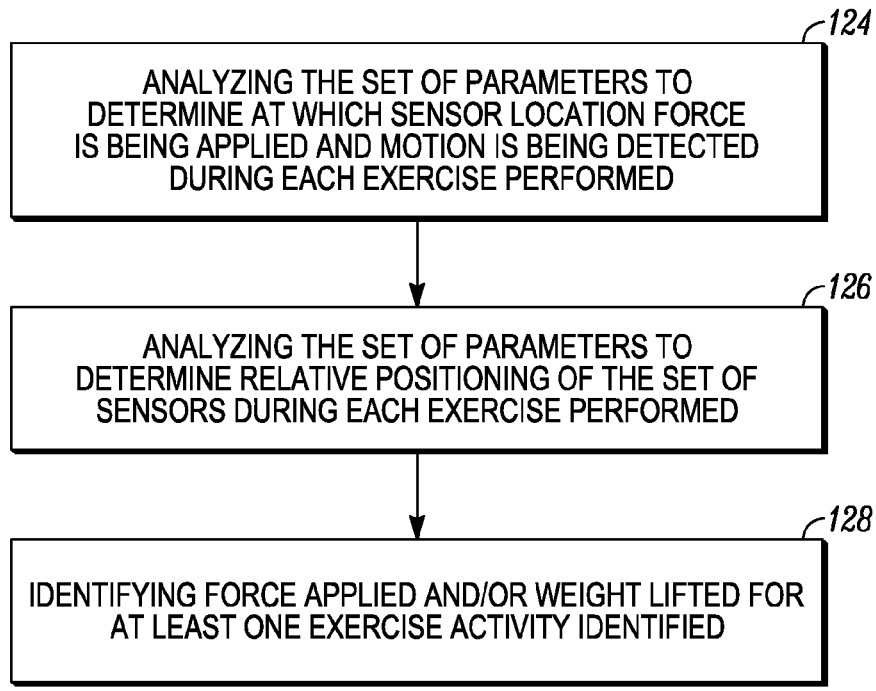
FIG. 9 is a flow diagram of process steps for analyzing a set of parameters in accordance with an embodiment.

Referring to FIG. 9, during the analyzing step 106 discussed above, the set of parameters may be analyzed in step 118 to determine at which sensor location force is being applied and motion is being detected during each exercise performed. In addition, the set of parameters may also be analyzed to determine relative positioning of the set of sensors during each exercise performed in step 120 and to identify force applied and/or weight lifted in step 122 for at least one exercise activity identified.

As stated above, workout routines may be performed under different priorities with respect to the performance of a task within a shortest period of time possible or performance of a task continually until the expiration of a predetermined period of time. Thus, although the same workout routine may be performed by an exerciser, recognition of what type of priority (task or time) placed on the workout routine is also important information that is automatically detected by the embodiments.

For purposes of example, a workout routine such as the above referenced FRAN workout routine can be performed having a task priority or a time priority within a fitness program. If the FRAN workout is performed as a task priority workout, the exerciser will typically complete the full pattern of exercises (i.e., task), as discussed above, one full time (or a predetermined number of full times) and will aim to accomplish this task in as short a period of time as possible. Thus, all of the exercises within a sequence are completed, and elapsed time needed to accomplish the full sequence is of significance when comparing results versus previous attempts to perform the task or the attempts of others.

In contrast, if the above referenced FRAN workout routine is performed as a time priority workout, the goal is to perform as many rounds as possible ("AMRAP")—that is, as many rounds of the sequence of exercises of the workout routine as possible—within a predetermined fixed period of time, e.g., 10 minutes, 20 minutes, or the like. In such a workout, the exerciser will attempt to complete the full sequence of exercises and will then immediately start over and repeat the same pattern or sequence of exercises as many times as possible before expiration of the fixed time period. Thus, in a time priority workout, for example, an exerciser may complete one full workout routine and have partially completed a second sequence upon expiration of the fixed time period. At the expiration of the time period, the exercise discontinues the exercise and the workout routine is finished. Accordingly, in a time priority workout, in many cases, the exerciser will not complete the last repetition of the pattern or sequence of exercises required for a full round of the workout routine due to termination of the exercise at the expiration of the fixed time deadline.

Figure 7:
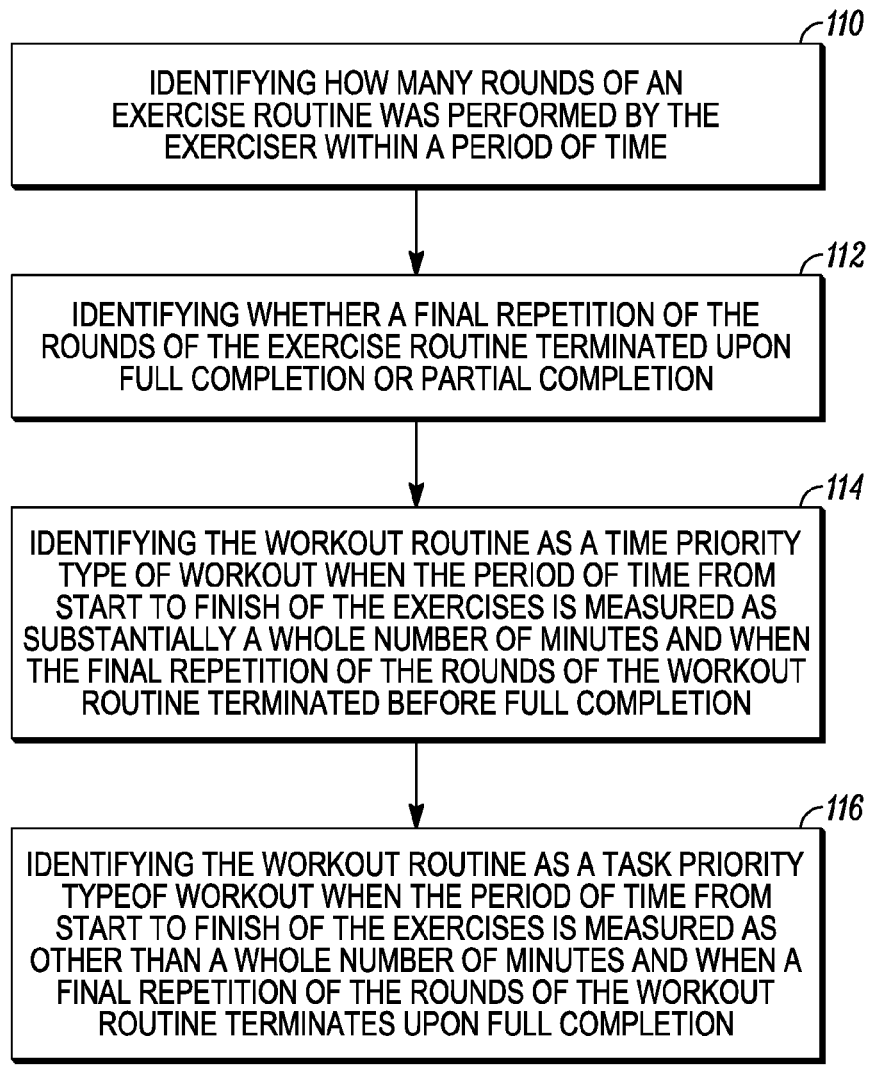
FIG. 7 is a flow diagram of process steps for analyzing a set of parameters used to distinguish between time priority and task priority workout routines in accordance with an embodiment.

According to embodiments, captured data is automatically analyzed to determine the workout routine as discussed above, the elapsed time of the activity from start to finish, and whether or not the activity finished upon completion of a full or partial sequence of exercises. Thus, in FIG. 7, the number of rounds that an exercise routine is performed by the exerciser within a period of time is automatically identified from the set of parameters captured by the sensors in step 110 and whether a final repetition of the rounds of the exercise routine terminated upon full completion or partial completion is automatically identified from the set of parameters captured by the sensors in step 112.

In a time priority workout, the detected time of the workout is likely to be a whole number of minutes, with some relatively minor margin of error (e.g., 9 minutes and 59 seconds, 15 minutes and 1 second, or the like). Thus, if elapsed time of the workout falls near a whole number of minutes and the final iteration of the workout includes only a partial accomplishment of the full sequence of exercises, the analysis identifies the workout routine and that it was performed as a time priority workout. See step 114 in FIG. 7. Data concerning how many times the full sequence of exercises of the workout routine was accomplished within the fixed time and how far into the final iteration of the sequence was achieved by the exerciser is also detected and recorded. See steps 110 and 112 of FIG. 7 discussed above. In contrast, if the detected workout time is not near a whole minute, such as a time of 6 minutes and 18 seconds, and if the exercise was terminated at the completion of a full sequence of exercises comprising the workout, the embodiments identify the activity as a task priority workout. See step 116 in FIG. 7.

Another example of a time priority workout is referred to as interval training. In the time priority workout example discussed above, the exerciser performs the sequence of exercises without intentional periods of rest during the fixed time period. However, in interval training, rest periods are provided within the workout routine. For instance, a first example of interval training is a workout directed to repeating an activity every minute on the minute ("EMOM"), for a specified number of minutes. An exerciser performs a prescribed pattern within a minute. If the pattern is completed in less than a minute, the exerciser is able to rest for the remainder of the minute, before starting the next repetition at the beginning of the next minute.

A second example of interval training is referred to as Tabata training. Tabata training is high-intensity intermittent training involving a rotation of short bursts of maximum effort followed by short periods of rest. For instance, a workout routine based on Tabata training may be performed for a total of four (4) minutes and may be divided into eight (8) intervals with each interval including twenty (20) seconds of high-intensity exercise followed by ten (10) seconds of rest. Tabata training plans are typically highly individualized and, as merely one example, a Tabata training plan might include: barbell squats during a first interval; push-ups during a second interval; barbell squats during a third interval; chin-ups during a fourth interval; push-ups during a fifth interval; chin-ups during a sixth interval; and sprinting in place during the seventh and eighth intervals.

Figure 8:
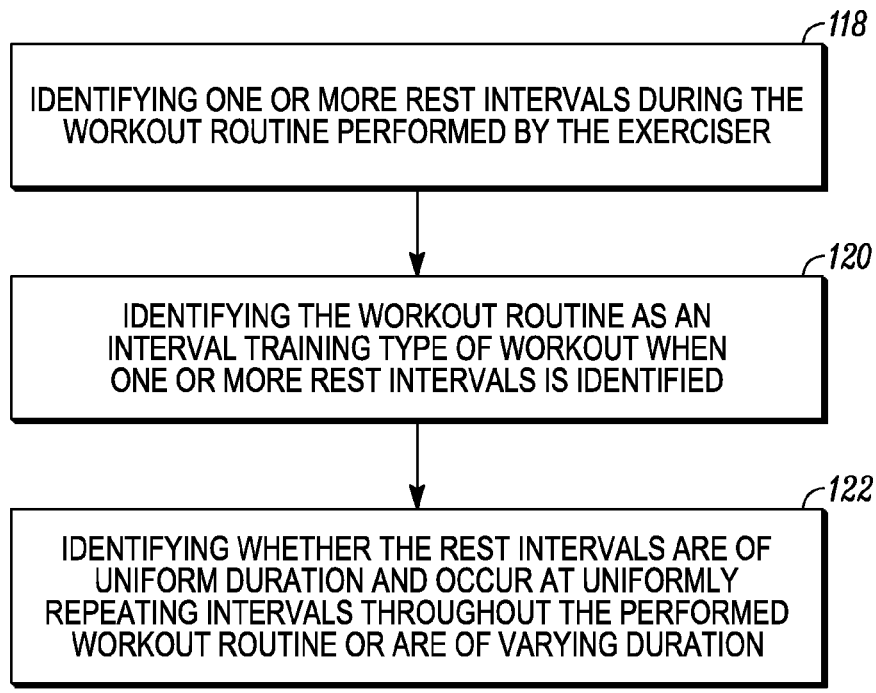
FIG. 8 is a flow diagram of process steps for analyzing a set of parameters to identify an interval training workout routine in accordance with an embodiment.

Accordingly, embodiments disclosed herein are able to determine whether or not a recognized workout routine is an interval training workout based on the recognition of rest periods during the workout sequence. For instance, according to the method steps shown in FIG. 8, one or more rest intervals during the workout routine performed by the exerciser are identified in step 118 based on analysis of the captured sensor data, and if one or more intervals are identified, the workout routine is identified as an interval training type of workout in step 120. In addition, in step 122, identification of whether the rest intervals are of uniform duration and occur at uniformly repeating intervals throughout the performed workout routine or are of varying duration is determined. Thus, not only is the workout routine and the time priority type of workout automatically recognized from the readings captured from the sensors, the workout being performed as an interval training workout is identified and whether the rest periods are fixed time periods as in Tabata training or merely result as remaining time within a repeating period of time.

For purposes of recognizing exercises, workout routines, and types of workouts discussed above, the sensors worn by the exerciser automatically communicate their readings to a central sensor or other device by wireless communications, for instance, via personal area network (e.g., Bluetooth) communications or other wireless communication technique. In addition, sensors can be provided on the exerciser for detecting an amount of weight lifted, for instance, during a free weight exercise. A force sensor such as a microstrain sensor may be used for this purpose. Motion and/or position sensors may be provide by position, acceleration, or gyroscopic sensors. Other types of sensors can also be utilized, for instance, medical sensors used to measure muscle using electrode, EMG, or the like, heart-rate sensors, Global Positioning Sensors (GPS), a barometric sensor or other sensor useful for determining change in terrain.

The sensors are worn on one or more specified locations on the body of the exerciser. For this purpose, the sensors may be built into, attached to, disposed on, or placed within apparel. For instance, the sensors may be permanently or removably fastened to apparel, may be woven or otherwise incorporated or built into apparel, and may be placed within a compartment or pocket of apparel. Such a pocket or compartment may be for general purpose or may be specially adapted to receive the sensor, and may or may not be open or closed. Examples of apparel may include handwear, footwear, clothing, headwear, neckwear, shoes, socks, compression wear, gym shorts, gloves, sections of gloves, thumb straps, finger straps, shirts, sleeves, straps, eyeglasses, earphones, earbuds, headsets, hearing aids, earpieces for one ear or both, hats, caps, helmets, pads (such as football pads), bands including armbands, wristbands, headbands, etc., belts, and the like. In some embodiments, apparel can include prosthetic and orthotic devices. As another alternative, in some embodiments, sensors can also be applied to the exerciser, or to the exerciser's other articles of apparel, via the use of adhesive patches, hook and loop fasteners, or the like.

FIG. 1 provides an example of an arrangement of a plurality of sensors that may be worn on the body 10 of an exerciser for the purposes described above. In FIG. 1, a force sensor 12 and a position sensor 14 may be worn on the thumb 16 of each hand 18 of the exerciser and a force sensor 20 and a position sensor 22 may be worn on the palm of each hand 18 of the exerciser. In addition, a force sensor 24 and a position sensor 26 may be worn on each arm of the exerciser adjacent each elbow 28. Further, a force sensor 30 and a position sensor 32 may be worn on the bottom of each foot 34 of the exerciser, and a force sensor 36 and position sensor 38 may be arranged in an upstanding and/or outward-facing position in front of the front or toes of each foot 34. A force sensor 40 may be worn adjacent the neck 42 of the exerciser, and a position sensor 44 may be worn on the trunk 46 or midsection of the exerciser. A personal hub device 48, discussed in greater detail below, may be worn on the trunk 46 or head 50 of the exerciser.

It should be understood that the above combination and arrangement of sensors on the body 10 of the exerciser is not limiting and can include any combination of sensors necessary to distinguish between different physical activities as desired. In some locations, only position sensors or only force sensors may be needed. Also, additional sensors and sensor locations can be utilized such as on one or more fingers, e.g., at the bottom third of the index finger or middle finger, of the hand of the exerciser, on the wrists, forearms, upper arms, shoulders, back or knees of the exerciser, and on the lateral sides and/or on the top of the feet of the exerciser. As other alternatives, sensors could be located on the front of the big toe facing in an anterior or outward direction (e.g., for detecting a kick or a push-up position). In further embodiments, sensors could be located at the bottom of the big toe, multiple sensors (e.g., in a line or array) could be positioned from one or more toes to the heel, or multiple sensors (e.g., in a line or array) could be positioned from the pad or tip of one or more fingers (or thumb) to the palm or to the wrist. As a further example, at least one sensor may be disposed on exercise apparel adapted to be positioned on at least one buttock of the exerciser. Such a sensor is able to provide readings useful for identifying exercises such as rowing, cycling, and sit-ups, and in detecting rest intervals during interval training, or a failure to complete a round of exercises due to exhaustion.

Figure 2:
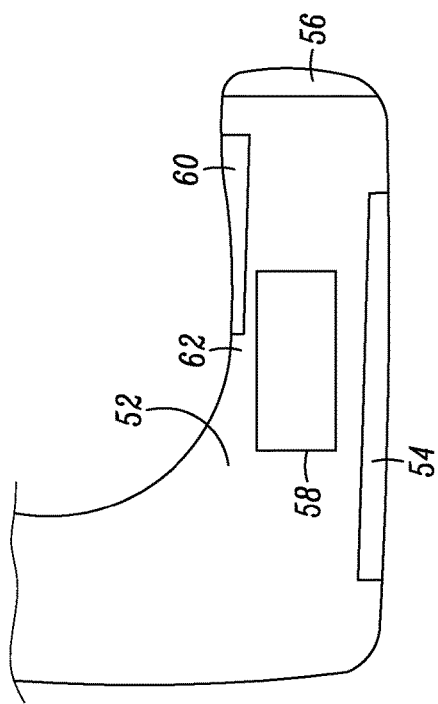
FIG. 2 is an elevational view of the footwear having an arrangement of sensors in accordance with an embodiment.

With respect to a specific example, FIG. 2 illustrates sensor positions on a foot 52 of an exerciser including position and/or force sensors 54 on the bottom of the foot 52, position and/or force sensors 56 in front of foot 52 disposed transversely or perpendicularly relative to the sensors 54 and facing in a forward or outward direction of the foot, a sensor 56 on the inner side 58 of the foot 52 of the exerciser such that it faces on opposed sensor on the opposite foot, and a sensor 60 on the front top 62 of the foot 52. With this arrangement of sensors, particularly sensors 56 and 60, on each foot of the exerciser, sensor data can be captured for use in identifying the exercise of rope climbing. In such an exercise, the exerciser can apply pressure by squeezing the rope between the inner side 58 of each foot and can apply pressure on the front top 62 of one foot with the bottom of the other foot. The presence/absence of these pressures relative to the above described sensors can be used to automatically detect rope climbing and/or to automatically distinguish rope-climbing from other physical activities.

In some embodiments, each sensor communicates its readings via wireless communications to a hub device, such as either hub device 48 shown in FIG. 1. Each sensor may send transmissions directly to the hub device or, alternatively, the sensors could communicate directly with a central sensor which communicates with the hub device or, as a further alternative, the sensors could communicate with each other (e.g., via a mesh communication technique). If a central sensor is utilized, it could be used to relay the captured sensor data to the hub device directly or to a mobile device that ultimately communicates with the hub device. As one example, the mobile device could be a smartphone on which an app (software application) is being run to receive and transfer sensor data.

Figure 3:
FIG. 3 is a diagram showing a flow of communication between wearable sensors worn on an exerciser to a remote server in accordance with an embodiment.

An example of communication flow in a configuration hereinafter referred to as a personal configuration could be as shown in FIG. 3. In this example, the various sensors 64 worn on the body of exerciser communicate readings to a central sensor 66 also worn on the body of the exerciser. The central sensor 66 relays all sensor data to a personal hub device 68 which then transfers all or some of the information to a server 70 connected to a cloud network 72 or the like. The personal hub device 68 may also receive information from the server 70 via a two-way communication link.

The pattern recognition analysis of the sensor data to identify an exercise, workout routine, and type (i.e., task priority, time priority, interval training, Tabata training, etc.) and the recording of performance data (i.e., time, applied force, etc.) may be performed by software stored on the server 70 or by software loaded on the personal hub 68 or both. One of these devices, 68 and 70, may be used to perform the analysis while the other is used to record historical data and/or make it available for review by the exerciser.

As an alternative to the personal configuration, FIG. 4 provides an example of communication flow that might be used in a so-called competitive configuration with direct communication between personal hubs of different exercisers, such as Person 1 and Person 2 (see FIG. 4). Here, the various sensors 74 worn on the body of an exerciser (Person 1 or Person 2) communicate readings to a central sensor 76 also worn on the body of the exerciser (Person 1 or Person 2). The central sensor 76 than relays all the captured data to a personal hub device, 78 for Person 1 and 80 for Person 2, which then transfers all the information to a server 82 on a cloud network 84 or the like. However, the personal hub 78 of Person 1 may also communicate with the personal hub 80 of Person 2 thereby permitting the possibility of competition between the exercisers. For example, an exerciser that performs a FRAN workout discussed above in a shortest period of time or with a greatest amount of weight or a combination of both may be indicated via such communications so that the results are shared between competitors.

A still further alternative is shown in FIG. 5 which provides an example of communication flow in a competitive configuration coordinated by a local hub 86 (e.g., at a facility such as a gym, track, etc., or in a home network having a local hub). Here, the various sensors 88 worn on the body of an exerciser communicate readings to a central sensor 90 also worn on the body of the exerciser. The central sensor 88 than relays all the captured data to a personal hub device 92 which then transfers all the information to the local hub 86 which in turn transfers information to a server 94 on a cloud network 96 or the like. In this embodiment, the results of Person 1 and Person 2 may be shared via communications with the local hub 86.

In the embodiment shown in FIGS. 3-5, the central sensor may be a wearable device such as worn on the trunk, belt, wrist, or arm of the exerciser in a position for receiving communications from the other sensors and in a position for transmitting captured sensor data to the personal hub device. The central sensor itself may include one or more specialized sensors that may not need to be duplicated among the other sensors (e.g., GPS, gyroscopic sensor, barometer, etc.). As an alternative, the central sensor and personal hub may be combined and included in a single wearable device. As another alternative, if each sensor worn by an exerciser is able to communicate directly with the personal hub, then the central sensor can be eliminated and is therefore optional.

Examples of personal hub devices include mobile devices running apps (software applications), smartphones, tablet computers, personal computers, or the like which are capable of connecting to a network or the like for the purpose of transferring, receiving, analyzing and/or storing data. The personal hub may or may not be worn on the exerciser. For instance, a personal hub provided by a smartphone may be secured in a pocket or the like of clothing worn by the exerciser or may just need to be within the vicinity and not necessarily worn. Alternatively, the central sensor may communicate with the personal hub at a later time after the performance of exercises or workout routines, such as when the exerciser returns home.

In a competitive environment, the set of sensors worn by each exerciser may be paired with their respective central sensor and/or personal hub device for association with one exerciser for purposes of distinguishing multiple exercisers from one another (e.g., when multiple exercisers' sensors are within range of a central sensor or personal hub).

The personal hub can be used to receive, store, and/or process data from sensors to capture performance data. Either the central sensor or the personal hub may include features to manage synchronization of communications among the multiple sensors. In one contemplated embodiment, the hub device may transmit the raw and/or processed data, in real-time or later, to a local hub and/or to the cloud (e.g., to one or more remote servers). As stated above, an example of a local hub may be a personal computer at a facility such as a gym, track, or other shared exercise venue, or in a home network.

The remote servers on the cloud or other network can be provided for purposes of dealing with functions such as authentication, user permissions, and privacy. The remote servers can also provide applications for recordkeeping, training, coaching, virtual competition, and the like. The analysis required for exercise identification can be performed in the personal or local hub. Alternatively, this function can be performed by the remote servers. Likewise, recordkeeping, reporting, and coaching functions can be performed at the personal and/or local hub or at the remote servers. In some contemplated embodiments, basic or limited functionality can be provided by the personal and/or local hub; while, more advanced functions may be provided by the remote server or servers.

Reports can be provided, e.g., for coaching, training, self-assessment, and the like. Reports may, for example, include text, graphs, tables, and the like and may provide automated performance tracking over time (e.g., a workout journal). In further embodiments, reporting and coaching may be provided in audio form to the exerciser during or after performance of an exercise or workout routine. For example, historical analysis can be provided such as "Last time, you did 1:52." In addition, real-time coaching can be provided (with or without an acceptable period of delay) such as "Faster! You are 3 seconds behind your last workout."

Individual users may be authenticated to the remote servers, and each sensor worn by the individual may include a unique identifier, such as a factory-preset numerical identifier. A personal or local hub can send an "authenticated" performance (e.g., an authenticated record of its readings for a period of time) to a collection point, such as on a remote server. In some implementations, GPS can be part of performance authentication. For example, GPS locations over time on a road or path, or GPS location at a gym, track, or other exercise facility, can be part of authenticating performance. Still further, a local hub may be registered as a trusted location, so a third party can have greater trust that the workout was performed as claimed. For example, a gym or other exercise facility may register its local hub, providing assurance that the data transmitted through the local hub actually represents exercises performed at the facility. Authenticated performance records can be provided, with the user's permission, to third parties such as the user's coach, fitness provider (e.g., gym), medical provider, or a facilitator of a competition.

An example of the use of authentication for a facilitated competition is one that requires, prior to participation, proof of ability to perform at a pre-determined level. Currently this may be provided by sending a video of one's performance; however, according to embodiments disclosed herein, an authenticated performance record generated as discussed above can be transmitted to establish proof of ability.

In a competitive environment, such as a race, tournament, or other type of competition, information about a competitor's real-time performance can be provided to other competitors. For example, multiple competitors may be using a shared local hub, or may only be using individual personal hubs. As part of a competition, the local hub or the remote servers can send each competitor's performance data to other competitors. In some embodiments, performance data may be synchronized with video, or may be used to generate a visual avatar of a competitor. "Real-time" performance data may lag video or actual real-time, but could synchronize periodically (e.g., at end of a round, set of repetitions, lap, milepost, or other interval), e.g., to say or indicate, "You are 3 seconds behind Joe after one round."

In the foregoing specification, specific embodiments have been described. However, one of ordinary skill in the art appreciates that various modifications and changes can be made without departing from the scope as set forth in the claims below. Accordingly, the specification and figures are to be regarded in an illustrative rather than restrictive sense.

We claim:

1. A system for automatically identifying performance of workout routines, comprising:

a set of sensors each being wearable at one or more specified locations on a body of an exerciser during a performance of a plurality of exercises, each one of the set of sensors configured to measure a parameter of one or more aspects of the performance during said performance, the parameter selected from a group consisting of motion, acceleration, position relative to one or more others of said set of sensors, and applied force, and each one of the set of sensors configured to communicate parameters measured; and a device configured to receive a set of parameters measured over a period of time by the set of sensors and configured to access stored pattern information corresponding to a plurality of predetermined exercise activities and a plurality of predetermined workout routines;

the device further configured, based on the stored pattern information and the set of parameters measured over at least a portion of the period of time, to identify one or more performed exercise activities performed by the exerciser during the period of time; and the device further configured, based on the stored pattern information and the performed exercise activities, to identify a performed workout routine performed by the exerciser during the period of time; and wherein the set of sensors includes at least one sensor disposed on footwear adapted to be worn on a foot of the exerciser, said at least one sensor disposed on footwear including a sensor adapted to be positioned in an outward-facing position for detecting bearing of weight associated with a prone position of the exerciser during the performance of a push-up, on a front of the footwear corresponding to front of toes of the exerciser.

2. A system according to claim 1, wherein the plurality of exercises comprises calisthenics and free-weight exercises.

3. A system according to claim 1, wherein the plurality of exercises is sequentially performed in one or more rounds, each round comprising one or more exercises.

4. A system according to claim 1, wherein each exercise of the plurality of exercises comprises one or more repetitions of an exercise pattern.

5. A system according to claim 4, wherein the device is further configured to identify how many times one of the plurality of predetermined workout routines was performed by the exerciser within the period of time and whether a final repetition of the exercise pattern terminated upon full completion or partial completion.

6. A system according to claim 1, wherein the device is further configured to identify the workout routine as a time priority workout when the period of time from start to finish of the plurality of exercises is measured as substantially a whole number of minutes and when a final repetition of one of the plurality of predetermined workout routines performed terminates before full completion.

7. A system according to claim 1, wherein the device is further configured to identify the workout routine as a task priority workout when the period of time from start to finish of the plurality of exercises is measured as other than a whole number of minutes and when a final repetition of one of the plurality of predetermined workout routines performed terminates upon full completion.

8. A system according to claim 1, wherein the device is further configured to identify one or more rest intervals between exercises.

9. A system according to claim 8, wherein the device is further configured to identify the performed workout routine as being an interval training workout when one or more rest intervals are identified within the performed workout routine.

10. A system according to claim 9, wherein the device is further configured to identify whether the one or more rest intervals are of uniform duration and occur at uniformly repeating intervals throughout the performed workout routine or are of varying duration.

11. A system according to claim 1, wherein the device is configured to identify at least one of effort exerted and weight lifted for at least one of the performed exercise activities identified.

12. A system according to claim 1, wherein the device is configured to analyze at least one of sensed position, applied force, motion and acceleration to automatically identify and distinguish among different exercises performed during the performed workout routine based on pattern recognition of the at least one of sensed position, applied force, motion and acceleration.

13. A system according to claim 12, wherein the device is configured to analyze said set of parameters to determine at which sensor location force is being applied and motion is being detected during an exercise.

14. A system according to claim 12, wherein the device is configured to analyze said set of parameters to determine relative positioning of said set of sensors during an exercise.

15. A system according to claim 12, wherein the device is configured to identify at least one of effort exerted, weight lifted, and number of repetitions completed for each exercise identified within the performed workout routine.

16. A system according to claim 1, wherein said set of sensors includes at least one sensor disposed on exercise apparel adapted to be positioned on at least one buttock of the exerciser for detecting a seated position during the performance.

17. A system according to claim 1, further comprising exercise apparel including handwear and footwear on which at least selected ones of said set of sensors are disposed on for being worn on hands and feet of the exerciser.

18. A system according to claim 17, wherein said exercise apparel further includes apparel on which at least one sensor of said set of sensors is disposed on for being worn on at least one of arms, trunk, and neck of the exerciser.

19. A system according to claim 1, wherein said set of sensors are disposed on exercise apparel selected from the group consisting of handwear, footwear, clothing, shirts, sleeves, pants, gym shorts, compression wear, gloves, sections of gloves, thumb straps, finger straps, straps, headwear, neckwear, eyeglasses, earphones, earbuds, headsets, hearing aids, earpieces, hats, caps, helmets, protective pads, bands, armbands, wristbands, headbands, belts, prosthetics, orthotic devices, shoes, socks, and adhesive pads.

20. A system according to claim 1, wherein said set of sensors includes at least one sensor disposed on handwear adapted to be worn on a hand of the exerciser, and wherein said at least one sensor disposed on handwear includes at least one sensor for measuring force applied and at least one sensor for monitoring motion or position relative to others of said set of sensors.

21. A system according to claim 20, wherein said at least one sensor disposed on handwear includes sensors adapted to be worn on a thumb of the hand of the exerciser for measuring force applied and for monitoring one of position and motion and sensors adapted to be located on a palm or base of a finger of the hand of the exerciser for measuring force applied and for monitoring one of position and motion.

22. A system according to claim 1, wherein said set of sensors includes at least one sensor attached to exercise apparel adapted to be worn on an arm or trunk of the body of the exerciser, said at least one sensor includes a sensor for monitoring one of position and motion relative to others of said set of sensors.

23. A system according to claim 1, wherein said set of sensors includes at least one sensor disposed on exercise apparel adapted to be worn on a neck of the body of the exerciser.

24. A system according to claim 1, wherein the device is an electronic personal hub wearable on the body of the exerciser during performance of a plurality of exercises and configured to receive wireless communications from at least one of said set of sensors to receive said set of parameters.

25. A system according to claim 1, further comprising an electronic personal hub wearable on the body of the exerciser during performance of the plurality of exercises, being configured to receive wireless communications from said set of sensors, and being configured to upload said set of parameters to the device, wherein the device is a remote device selected from a group consisting of a smartphone, a computer, a server, and an electronic tablet.

26. A system according to claim 25, wherein the electronic personal hub is a central sensor which is included within said set of sensors.

27. A system according to claim 25, wherein said electronic personal hub is configured to manage synchronization of communications from said set of sensors.

28. Exercise apparel for use in automatically identifying performance of workout routines, comprising an article of footwear carrying a set of sensors each being wearable on a foot of an exerciser during a performance of a sequence of exercises comprising a workout routine, each being configured to measure a parameter of one or more aspects of the performance during said performance, the parameter selected from a group consisting of motion, acceleration, position, and applied force, and each being configured to wirelessly communicate parameters measured;
at least one of said set of sensors being carried on the footwear in an outward-facing position for detecting bearing of weight associated with a prone position of the exerciser during the performance, the outward-facing position being at a front of the footwear corresponding to front of toes of the exerciser;
wherein said at least one of said set of sensors carried on the footwear is for detecting the prone position during the performance of a push-up.

29. Exercise apparel according to claim 28, wherein the article of footwear is selected from a group consisting of a shoe, a sock, a strap, and an adhesive pad.

30. A method for automatically identifying performance of workout routines, comprising the steps of:
in one or more computer processors, measuring a set of parameters with a set of sensors each being worn at locations on a body of an exerciser during performance of a plurality of exercises, each one of the set of sensors configured to measure a parameter of one or more aspects of the performance during said performance, the parameter selected from a group consisting of motion, acceleration, position relative to one or more others of said set of sensors, and applied force, and each one of the set of sensors configured to communicate parameters measured;
in the one or more computer processors, communicating a set of parameters measured over a period of time by the set of sensors during said measuring step to a computing device configured to access stored pattern information corresponding to a plurality of predetermined exercise activities and a plurality of predetermined workout routines; and
in the computing device, analyzing the set of parameters via pattern recognition by one or more processors of the computing device, to identify one or more performed exercise activities performed by the exerciser during the period of time and to identify a performed workout routine performed by the exerciser during the period of time;
wherein at least one of said set of sensors is carried on the footwear in an outward-facing position for detecting bearing of weight associated with a prone position of the exerciser during the performance, the outward-facing position being at a front of the footwear corresponding to front of toes of the exerciser; and
wherein said at least one of said set of sensors carried on the footwear is for detecting the prone position during the performance of a push-up.

31. A method according to claim 30, further comprising the step of automatically and electronically recording data corresponding to each of the performed exercise activities and the performed workout routine identified by the computing device during said analyzing step.

32. A method according to claim 30, wherein the performed exercise routine comprises calisthenic and free-weight exercises which are sequentially performed in one or more rounds, each round comprising one or more exercises.

33. A method according to claim 32, wherein said analyzing step includes identifying how many rounds of the performed exercise routine was performed by the exerciser within the period of time and identifying that a final repetition of a round of the performed exercise routine terminated upon full completion or partial completion.

34. A method according to claim 32, wherein said analyzing step includes identifying the workout routine as a time priority workout when the period of time from start to finish of the plurality of exercises is measured as substantially a whole number of minutes and when a final repetition of one of the plurality of predetermined workout routines performed terminates before full completion.

35. A method according to claim 32, wherein said analyzing step includes identifying the workout routine as a task priority workout when the period of time from start to finish of the plurality of exercises is measured as other than a whole number of minutes and when a final repetition of one of the plurality of predetermined workout routines performed terminates upon full completion.

36. A method according to claim 30, wherein said analyzing step includes identifying one or more rest intervals during the performed workout routine.

37. A method according to claim 36, wherein said analyzing step includes identifying the performed workout routine as being an interval training workout when one or more rest intervals are identified.

38. A method according to claim 37, wherein said analyzing step includes identifying whether the rest intervals are of uniform duration and occur at uniformly repeating intervals throughout the performed workout routine or are of varying duration.

39. A method according to claim 30, wherein said analyzing step includes identifying at least one of force applied and weight lifted for at least one of the performed exercise activities identified.

40. A method according to claim 30, wherein said analyzing step includes identifying at least one of sensed position, applied force, motion and acceleration to automatically identify and distinguish among different exercises performed during the performed workout routine based on pattern recognition of the at least one of sensed position, applied force, motion and acceleration.

41. A method according to claim 30, wherein, during said analyzing step, the device analyzes the set of parameters to determine at which sensor location force is being applied and motion is being detected during each exercise of the performed workout routine.

42. A method according to claim 30, wherein, during said analyzing step, the device analyzes the set of parameters to determine relative positioning of the set of sensors during each exercise of the performed workout routine.

43. A method according to claim 30, wherein the device is a personal hub wearable on the body of the exerciser and is configured to receive wireless communications from at least one of the set of sensors to receive the set of parameters.

44. A method according to claim 30, further comprising the steps of receiving wireless communications from the set of sensors with a personal hub worn on the exerciser during performance of the plurality of exercises, and uploading the set of parameters from the personal hub to the device, wherein the device is selected from a group consisting of a smartphone, a computer, a server, and an electronic tablet.

* * * * *